US012758134B2

(12) United States Patent
Davies et al.

(10) Patent No.: US 12,758,134 B2
(45) Date of Patent: Oct. 13, 2026

(54) MEDICAL DILATOR, AND SYSTEMS, METHODS, AND KITS FOR MEDICAL DILATION

(71) Applicant: Boston Scientific Medical Device Limited, Galway (IE)

(72) Inventors: Gareth Davies, Toronto (CA); Lauren Koon, Mississauga (CA); John Paul Urbanski, Toronto (CA); Eduardo Moriyama, Toronto (CA)

(73) Assignee: Boston Scientific Medical Device Limited, Galway (IE)

( * ) Notice: Subject to any disclaimer, the term of this patent is extended or adjusted under 35 U.S.C. 154(b) by 483 days.

(21) Appl. No.: 18/351,704

(22) Filed: Jul. 13, 2023

(65) Prior Publication Data

US 2023/0355155 A1 Nov. 9, 2023

Related U.S. Application Data

(63) Continuation of application No. PCT/IB2021/050266, filed on Jan. 14, 2021.

(51) Int. Cl.
*A61B 5/287* (2021.01)
*A61M 29/00* (2006.01)

(52) U.S. Cl.
CPC ............ *A61B 5/287* (2021.01); *A61M 29/00* (2013.01)

(58) Field of Classification Search
CPC ....... A61B 5/283; A61B 5/287; A61B 5/6855; A61B 2562/125; A61B 2562/22; A61B 18/1492; A61B 2018/00839
See application file for complete search history.

(56) References Cited

U.S. PATENT DOCUMENTS 5,500,012 A * 3/1996 Brucker ................ A61B 18/24 606/7
8,019,401 B1 9/2011 Smith et al.
(Continued)

FOREIGN PATENT DOCUMENTS

EP 2996755 B1 12/2020
JP 2006-525072 A 11/2006
(Continued)

OTHER PUBLICATIONS

EPD Solutions, a Philips company, Imaging beyond the catheter KODEX-EPD Cardiac Imaging and Mapping System, Jun. 2020, p. 1-4, https://images.philips.com/is/content/PhilipsConsumer/Campaigns/HC20200727_EPD_Solutions/EPD_Solutions_KODEX_EPD_Brochure.pdf (Year: 2020).*
International Search Report for PCT Application No. PCT/IB2021/050266 mailed Oct. 12, 2021. 7 pages.
Extended European Search Report and Search Opinion received for European Application No. 21919211.9, mailed on Sep. 4, 2024, 8 pages.

(Continued)

*Primary Examiner* — Eun Hwa Kim
(74) *Attorney, Agent, or Firm* — Nelson Mullins Riley & Scarborough LLP

(57) ABSTRACT

A medical dilator includes an elongate member having a proximal end portion, an opposed distal end portion, and a lumen extending through the elongate member from the proximal end portion to the distal end portion. A dilating tip is at the distal end portion. The dilating tip has a first end of enlarged cross-sectional area and tapers going in the distal direction to a second end of reduced cross-sectional area. At least a first electrode is associated with the dilating tip. An electrical conductor is electrically connected to the first electrode and extends proximally from the first electrode towards the proximal end portion for electrical connection with an electroanatomical mapping system.

11 Claims, 10 Drawing Sheets

(56) References Cited

U.S. PATENT DOCUMENTS

| | | | | |
|---|---|---|---|---|
| 10,493,259 | B2 | 12/2019 | Urbanski et al. | |
| 2003/0060822 | A1 | 3/2003 | Schaer et al. | |
| 2006/0089691 | A1 | 4/2006 | Kaplan et al. | |
| 2008/0103400 | A1* | 5/2008 | Krishnan | A61B 5/05<br>607/74 |
| 2010/0217257 | A1* | 8/2010 | Howat | B32B 37/1284<br>606/41 |
| 2010/0228202 | A1* | 9/2010 | O'Dea | A61M 25/1027<br>156/60 |
| 2014/0206987 | A1* | 7/2014 | Urbanski | A61B 18/1492<br>600/431 |
| 2015/0094795 | A1 | 4/2015 | Ginn et al. | |
| 2015/0250424 | A1 | 9/2015 | Govari et al. | |
| 2017/0079541 | A1 | 3/2017 | Krishnan | |
| 2020/0008883 | A1 | 1/2020 | Moak et al. | |
| 2020/0060710 | A1 | 2/2020 | Urbanski et al. | |

FOREIGN PATENT DOCUMENTS

| | | | | |
|---|---|---|---|---|
| JP | 2008-531221 | A | 8/2008 | |
| JP | 2008-237620 | A | 10/2008 | |
| JP | 2017-510410 | A | 4/2017 | |
| JP | 2017-512569 | A | 5/2017 | |
| JP | 2022-541393 | A | 9/2022 | |
| WO | WO-2004026134 | A1 * | 4/2004 | A61M 25/0662 |
| WO | 2018165277 | A1 | 9/2018 | |

OTHER PUBLICATIONS

Notice of Reasons for Refusal received for Japanese Patent Application No. 2023-542804, mailed on May 28, 2024, 6 pages (3 pages of English Translation and 3 pages of Original Document).

* cited by examiner

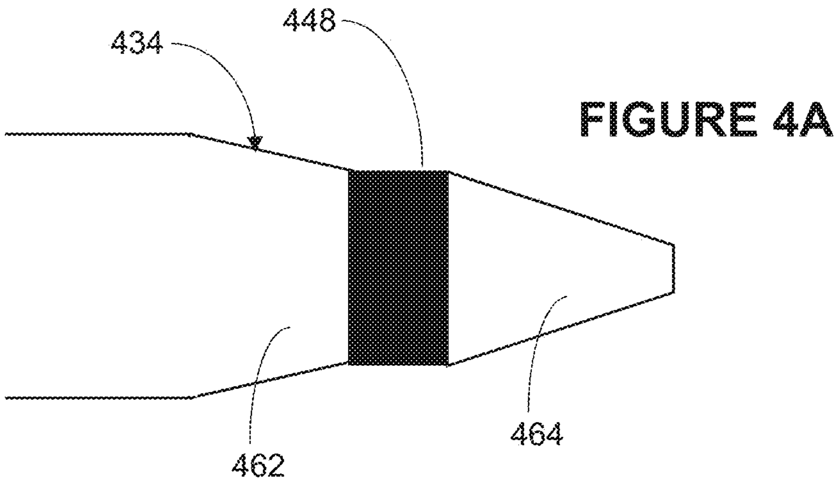
FIGURE 4A
FIGURE 4B
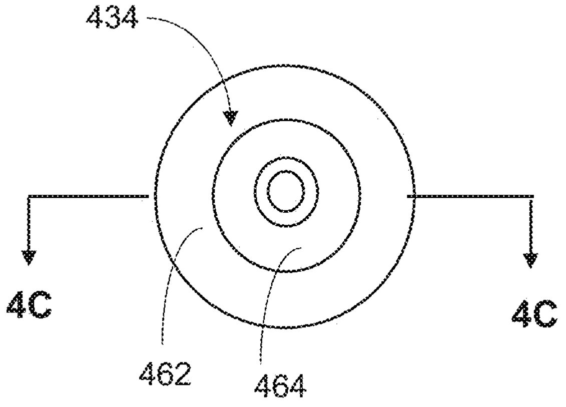
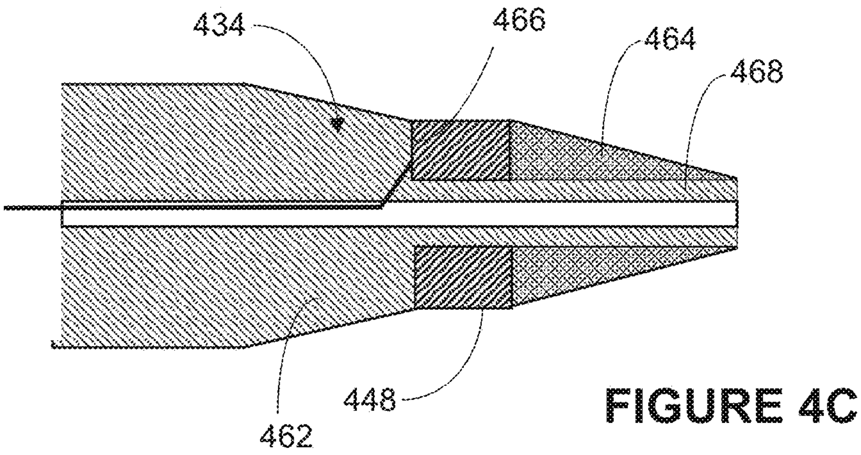
FIGURE 4C

MEDICAL DILATOR, AND SYSTEMS, METHODS, AND KITS FOR MEDICAL DILATION

CROSS REFERENCE TO RELATED APPLICATION

This application is a continuation application of International Application No. PCT/IB2021/050266, filed Jan. 14, 2021, titled "MEDICAL DILATOR, AND SYSTEMS, METHODS, AND KITS FOR MEDICAL DILATION," the entire disclosure of which is incorporated herein by reference.

FIELD

This document relates to medical dilation, for example dilation of a surgically created perforation in cardiac tissue. More specifically, this document relates to a medical dilator, and related systems, methods, and kits.

SUMMARY

The following summary is intended to introduce the reader to various aspects of the detailed description, but not to define or delimit any invention.

According to some aspects, a medical dilator includes an elongate member having a proximal end portion, an opposed distal end portion, and a lumen extending through the elongate member from the proximal end portion to the distal end portion. A dilating tip is at the distal end portion. The dilating tip has a first end of enlarged cross-sectional area and tapers going in the distal direction to a second end of reduced cross-sectional area. At least a first electrode is associated with the dilating tip. An electrical conductor is electrically connected to the first electrode and extends proximally from the first electrode towards the proximal end portion for electrical connection with an electroanatomical mapping system.

In some examples, the first electrode is positioned between the first end of the dilating tip and the second end of the dilating tip. In some examples, the first electrode is positioned proximal of the first end of the dilating tip.

In some examples, the dilating tip has a tip circumferential outer surface having a circumferential groove defined therein, and the electrode is annular and is seated in the groove.

In some examples, the dilating tip has a tip circumferential outer surface, a tip circumferential inner surface, and a tip sidewall extending between the tip circumferential inner surface and the tip circumferential outer surface, and the electrical conductor extends from the electrode through the tip sidewall and into the lumen.

In some examples, the elongate member has a circumferential outer surface, a circumferential inner surface, and a sidewall extending along the length of the elongate member between the circumferential inner surface and the circumferential outer surface, and the electrical conductor is embedded in the sidewall and extends from the electrode to the proximal end portion. The circumferential outer surface can have a longitudinal groove defined therein and extending from the first electrode to the proximal end portion, and the electrical conductor can be seated in the longitudinal groove. Alternatively, the elongate member can include an outer tube defining the circumferential outer surface, and an inner liner within the outer tube and defining the circumferential inner surface, and the electrical conductor can be positioned between the outer tube and the inner liner. The electrical conductor can be a tubular braid.

In some examples, the first electrode is removable from the elongate member.

In some examples, the medical dilator further includes a second electrode mounted to the elongate member and spaced from the first electrode.

In some examples, the dilating tip includes a proximal piece having a distal-facing shoulder surface and a neck extending distally from the shoulder surface, the electrode is annular and is received on the neck and abuts the shoulder surface, and the dilating tip further includes a distal piece received on the neck distally of and abutting the electrode.

In some examples, the first electrode forms the dilating tip. The medical dilator can include a metallic member that has a first section and a second section, and the first section can join the metallic member to the elongate member while the second section can provide the first electrode and the dilating tip.

In some examples, the electrode is radiopaque. In some examples, the electrode includes platinum-iridium.

In some examples, the electrode has an echogenic profile. In some examples the electrode includes a coil.

According to some aspects, a kit of parts for medical perforation system includes a medical dilator, a sheath, and a perforation device. The medical dilator has an elongate member having a proximal end portion, an opposed distal end portion, and a lumen extending through the elongate member from the proximal end portion to the distal end portion. The medical dilator further has a dilating tip at the distal end portion, and the dilating tip has first end of enlarged cross-sectional area and tapers going in the distal direction to a second end of reduced cross-sectional area. The medical dilator further has at least a first electrode associated with the dilating tip, and an electrical conductor electrically connected to the first electrode and extending proximally from the first electrode to the proximal end portion for electrical connection with an electroanatomical mapping system. The sheath is for receiving the medical dilator. The perforation device is receivable in the lumen.

In some examples, the kit of parts further includes at least a second electrode. The second electrode can be secured to the sheath, or secured to the elongate member, or secured to the perforation device.

In some examples, the sheath has a tip, the medical dilator further includes a second electrode that is electrically connectable to the electroanatomical mapping system, and when the medical dilator is fully inserted into the sheath, the second electrode is proximate the tip of the sheath.

According to some aspects, a medical dilation system includes a medical dilator and an electroanatomical mapping system. The medical dilator includes an elongate member having a proximal end portion, an opposed distal end portion, and a lumen extending through the elongate member from the proximal end portion to the distal end portion. A dilating tip is at the distal end portion. The dilating tip has a first end of enlarged cross-sectional area, and tapers going in the distal direction to a second end of reduced cross-sectional area. At least a first electrode is associated with the dilating tip, and an electrical conductor is electrically connected to the first electrode and extends proximally from the first electrode to the proximal end portion. The electroanatomical mapping system is electrically connectable to the electrical conductor and is configured to receive an electroanatomical mapping signal from the electrode and determine a location of the dilating tip based on the electroanatomical mapping signal.

In some examples, the electroanatomical mapping system is a dielectric open source system.

According to some aspects, a method for medical dilation includes a. advancing a dilating tip of a medical dilator towards a first target anatomical location; b. receiving a first electroanatomical mapping signal from an electrode associated with the dilating tip; and c. based on the first electroanatomical mapping signal, determining a first location of the dilating tip with respect to the first target anatomical location.

In some examples, after step c., the method further includes: d. advancing a perforation device out of the medical dilator, and creating a perforation in the first target anatomical location using the perforation device.

In some examples, the method further includes determining a location of the perforation device with respect to the dilating tip.

In some examples, after step d., the method further includes: e. advancing the electrode and the dilating tip through the perforation, to dilate the perforation.

In some examples, after or during step e., the method further includes: f. receiving a second electroanatomical mapping signal from the electrode, and g. based on the second electroanatomical mapping signal, determining a second location of the dilating tip with respect to the first target anatomical location. In some examples, the first target anatomical location is an atrial septum.

In some examples, the method further includes determining a location of the dilating tip with respect to a left atrial wall.

In some examples, step a. includes positioning the dilator within a sheath and advancing the dilator and the sheath towards the first target anatomical location, and the method further includes determining a location of the dilating tip with respect to a tip of the sheath.

In some examples, the method further includes receiving a second electroanatomical mapping signal from the electrode, and using the second electroanatomical mapping signal to create an anatomical map. The anatomical map can include at least one of a map of a superior vena cava, a map of a right atrium, and a map of pulmonary veins.

BRIEF DESCRIPTION OF THE DRAWINGS

The accompanying drawings are for illustrating examples of articles, methods, and apparatuses of the present disclosure and are not intended to be limiting. In the drawings:

FIG. 4A is an enlarged view of another example dilating tip;

FIG. 4B is an end view of the dilating tip of FIG. 4A;

FIG. 4C is a cross-section taken along line 4C-4C in FIG. 4B;

DETAILED DESCRIPTION

Various apparatuses or processes or compositions will be described below to provide an example of an embodiment of the claimed subject matter. No example described below limits any claim and any claim may cover processes or apparatuses or compositions that differ from those described below. The claims are not limited to apparatuses or processes or compositions having all of the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Generally disclosed herein are medical dilators (also referred to herein simply as "dilators") that can be used for dilation of anatomical apertures, such as surgical perforations. For example, the dilators can be used in transseptal perforation procedures, in which a perforation is created in the atrial septum of the heart, optionally using a radiofrequency perforation device, and then dilated using a dilator. Such procedures can be carried out, for example, to gain access to the left atrium for a medical treatment.

In general, the dilators disclosed herein are configured to allow for non-fluoroscopic visualization and determination of the location of the tip of the dilator (also referred to herein as the "dilating tip") within the body, or of the location of the tip of the dilator with respect to other surgical tools (e.g. with respect to the perforation device or with respect to a sheath in which the dilator is housed). More specifically, the dilators disclosed herein can include at least one electrode associated with the tip thereof. The electrode can be an electroanatomical mapping (EAM) electrode. The EAM electrode can be connected to an EAM system, which can communicate EAM signals to and from the EAM electrode (either directly or via a pad), and based on the EAM signals received from the EAM electrode, can determine a location of the EAM electrode, and thus the tip of the dilator, within the body or with respect to other surgical tools. This can, for example, visualize the dilator tip to allow a user to determine whether the tip is positioned properly with respect to a target tissue, allow a user to confirm that the perforation device is shrouded within the dilator prior to perforation, and/or allow for a user to confirm that the dilating tip is sufficiently spaced from non-target tissues.

Figure 1:
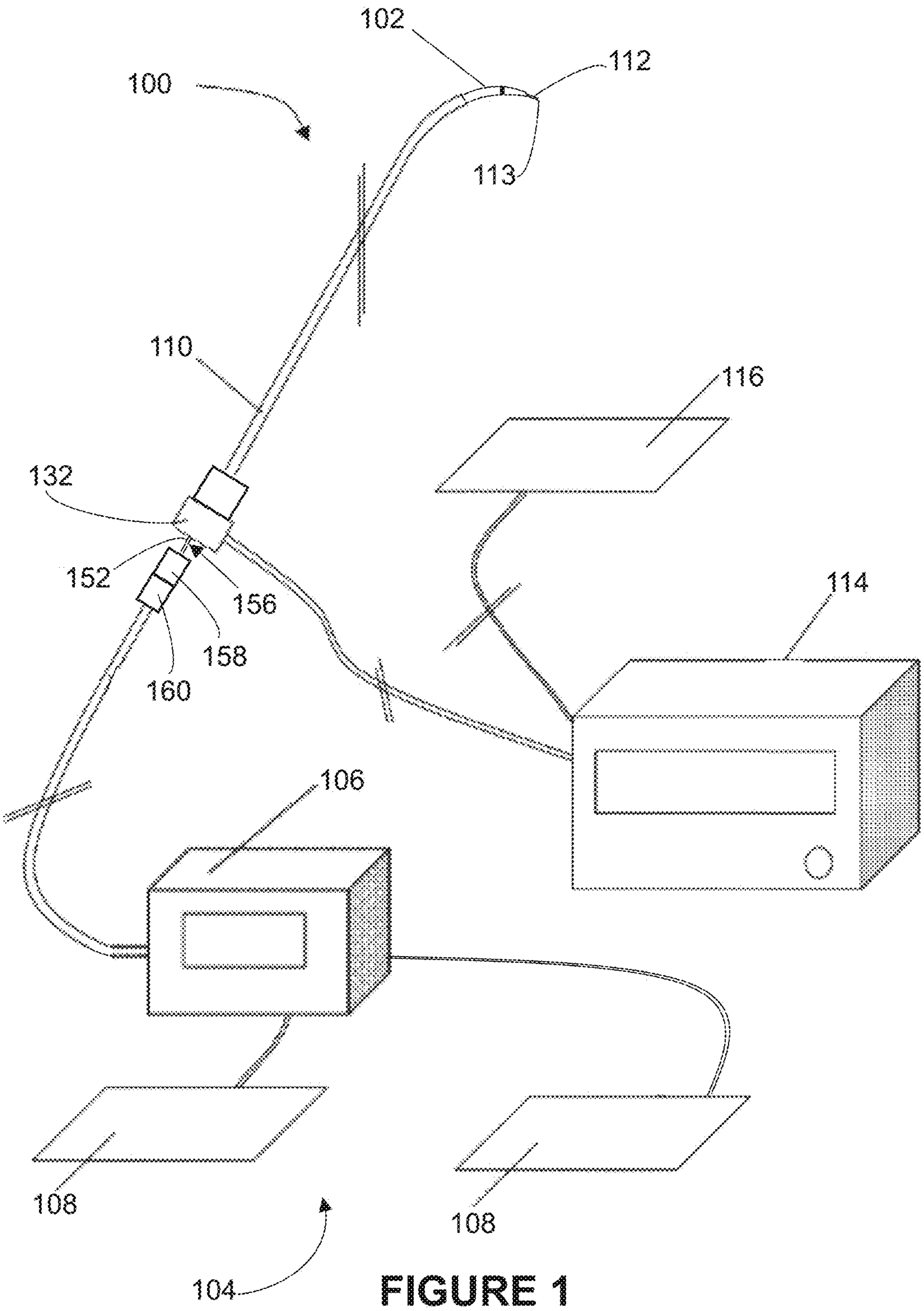
FIG. 1 is a perspective view of an example surgical perforation system.

Referring now to FIG. 1, an example surgical perforation system 100 is shown. The surgical perforation system 100 includes a dilator 102, an EAM system 104 including an EAM signal generator 106 and a set (e.g. 3 or more) of EAM pads 108 (only two of which are shown in FIG. 1), a sheath 110, a radiofrequency (RF) perforation device 112 having a perforation electrode 113 at its distal tip, and an RF generator 114 and grounding pad 116. The sheath 110, RF perforation device 112, RF generator 114, and grounding pad 116 will not be described in detail herein, and can optionally be those sold by Baylis Medical Company, Inc. (Montreal, Canada), for example under the brand names NRG® Transseptal Platform, or SupraCross® Transseptal Platform. Furthermore, in alternative examples, another type of perforation device, such as a mechanical perforation device, can be used instead of an RF perforation device. Optionally, some or all of the parts of the surgical perforation system 100 can be sold or provided together in a kit, either in an assembled state or in an unassembled state.

Figure 2:
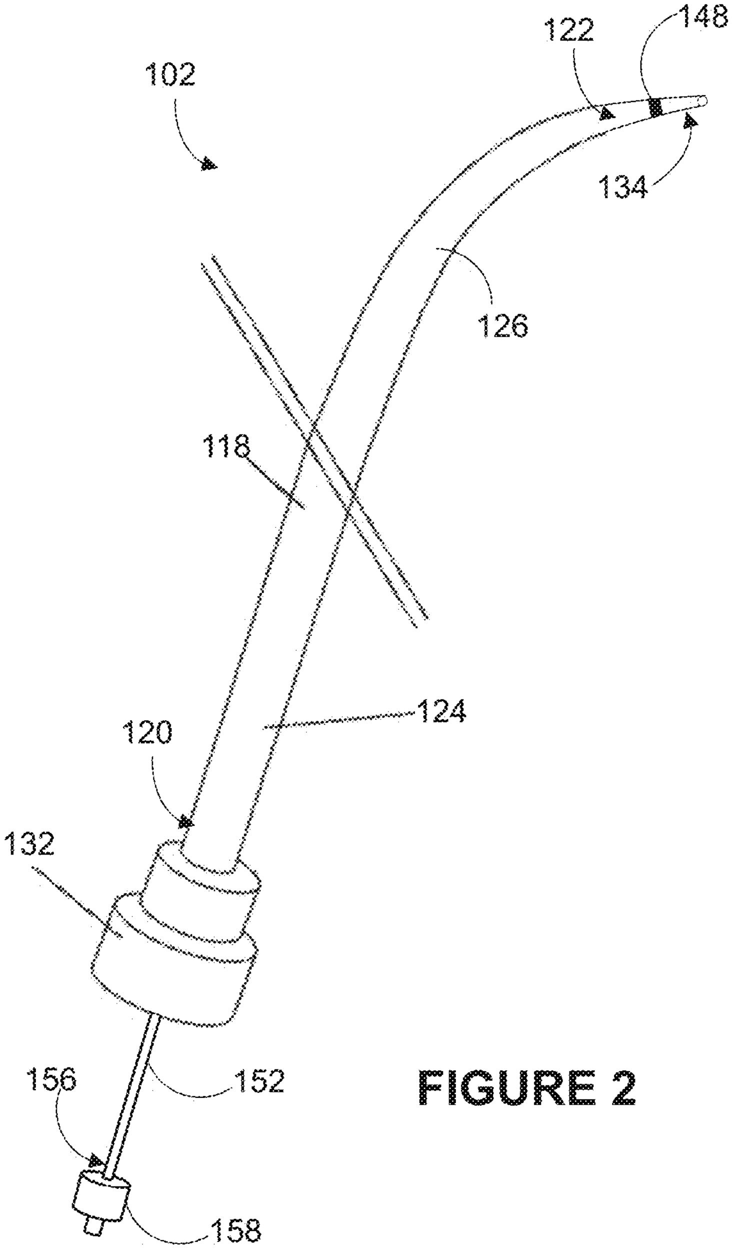
FIG. 2 is a perspective view of the dilator of the surgical perforation system of FIG. 1.

Referring now to FIG. 2, the dilator 102 is shown in greater detail. In the example shown, the dilator 102 includes an elongate member 118 having a proximal end portion 120, which in use is generally directed towards a user such as a surgeon, and an opposed distal end portion 122, which in use is generally directed towards a target location in a patient. The elongate member 118 includes a sidewall 124, which extends longitudinally between the proximal end portion 120 and the distal end portion 122, and radially between a circumferential outer surface 126 and a circumferential inner surface 128 (shown in FIGS. 3B and 3C). The circumferential inner surface 128 defines a lumen 130 (shown in FIGS. 3B and 3C), which extends through the elongate member 118 from the proximal end portion 120 to the distal end portion 122. In use, the lumen 130 can receive the RF perforation device 112.

The elongate member can be made from various materials, including but not limited to plastics such as high-density polyethylene (HDPE).

Referring still to FIG. 2, in the example shown, a handle 132 is mounted to the proximal end portion 120. The handle 132 can include various hubs and/or ports and/or connection points (not shown) for connection to various external devices.

Referring still to FIG. 2, the dilator 102 includes a dilating tip 134 at the distal end portion 122. The dilating tip 134 is shown in greater detail in FIGS. 3A to 3C.

Figure 3A:
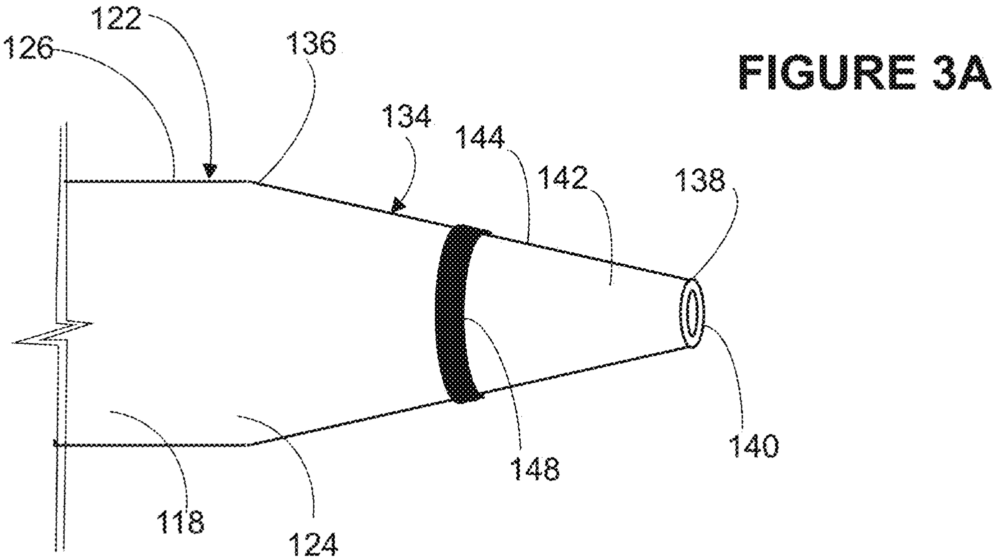
FIG. 3A is an enlarged view of the dilating tip of the dilator of FIG. 2.
Figure 3B:
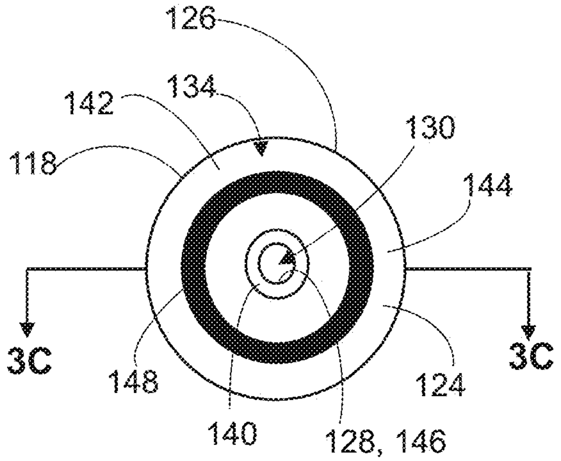
FIG. 3B is an end view of the dilating tip of FIG. 3A.
Figure 3C:
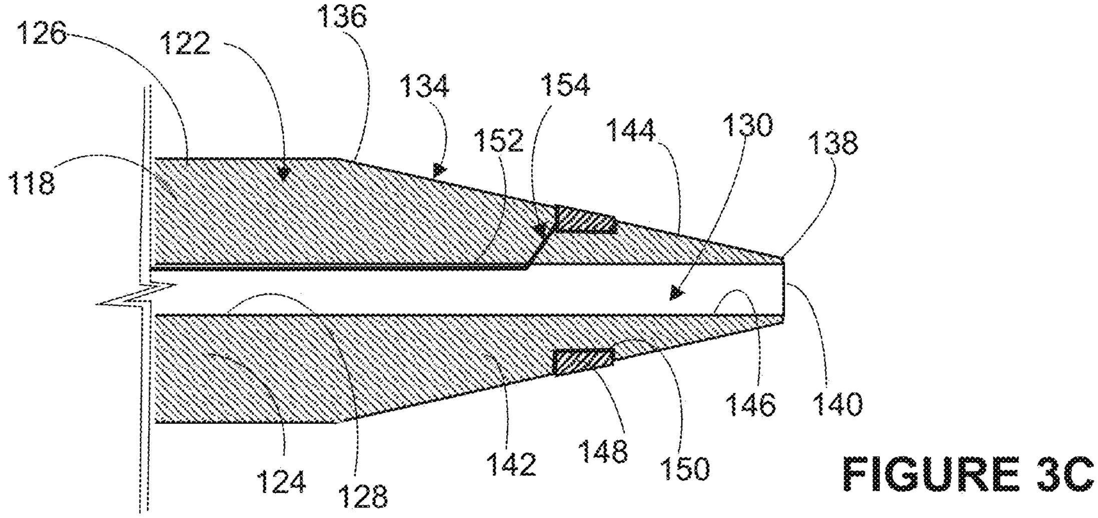
FIG. 3C is a cross-section taken along line 3C-3C in FIG. 3B.
Figure 5A:
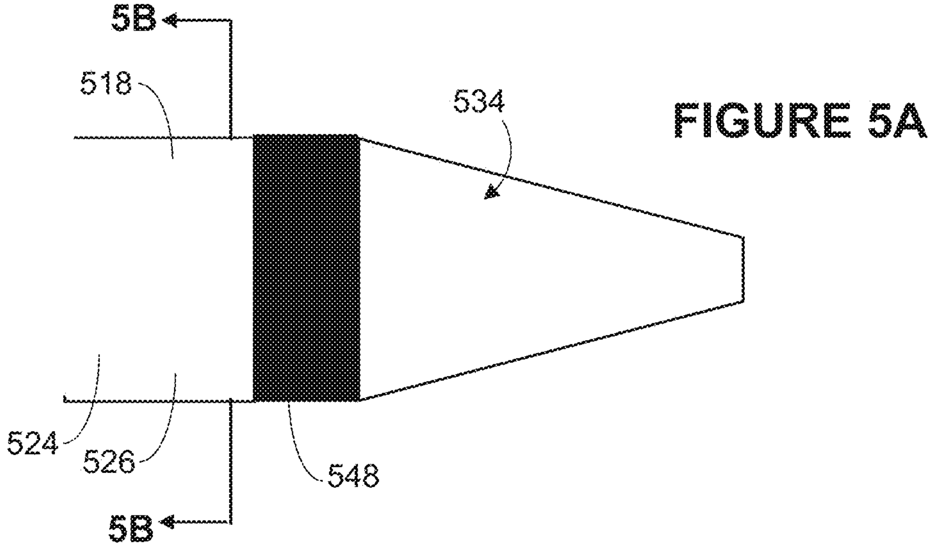
FIG. 5A is an enlarged view of another example dilating tip.
Figure 5B:
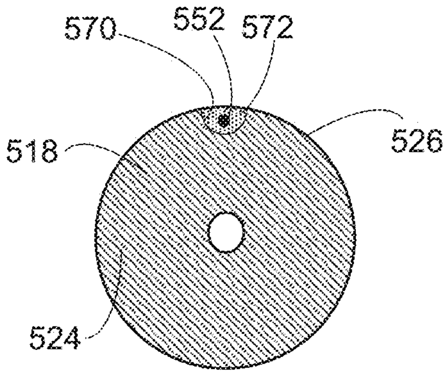
FIG. 5B is a cross-section taken along line 5B-5B in FIG. 5A.
Figure 5C:
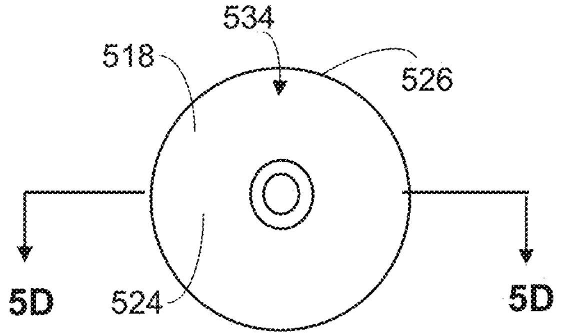
FIG. 5C is an end view of the dilating tip of FIG. 5A.
Figure 5D:
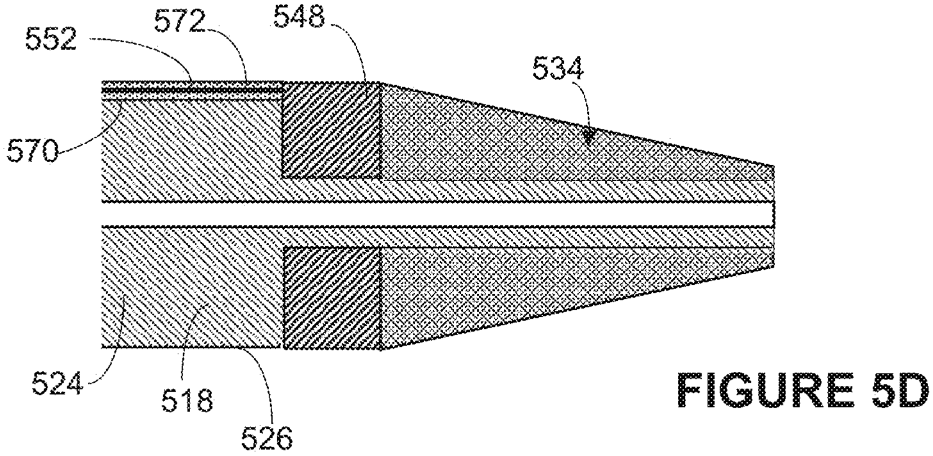
FIG. 5D is a cross-section taken along line 5D-5D in FIG. 5C.

All or a portion of the dilating tip 134 can be integral with the elongate member 118. That is, the distal end portion 122 of the elongate member 118 can include the dilating tip 134, as shown in FIGS. 3A to 3C. Alternatively, the dilating tip 134 can be a separate piece from the elongate member 118 and can be joined to the distal end portion 122 of the elongate member 118, as described below with respect to FIGS. 14A to 14C.

In the example shown, the dilating tip 134 includes a first end 136 and a second end 138 that is spaced distally from the first end 136. The dilating tip 134 tapers in cross-sectional area going from the first end 136 to the second end 138, so that the first end 136 has an enlarged cross-sectional area with respect to the second end 138, and the second end 138 has a reduced cross-sectional area with respect to the first end 136. As the dilating tip 134 is passed through an aperture, the enlargement in cross-sectional area dilates the aperture.

In the example shown, the second end 138 of the dilating tip 134 forms a distal end 140 of the dilator 102. In alternative examples (not shown), the dilating tip can be spaced proximally from the distal end of the dilator.

Referring still to FIGS. 3A to 3C, in the example shown, the dilating tip 134 has a sidewall 142 (also referred to herein as a "tip sidewall"), which extends longitudinally between the first end 136 of the dilating tip 134 and the second end 138 of the dilating tip 134, and radially between an circumferential outer surface 144 of the dilating tip 134 (also referred to herein as a 'tip circumferential outer surface") and an circumferential inner surface 146 of the dilating tip 134 (also referred to herein as a 'tip circumferential inner surface'). The tip sidewall 142, tip circumferential outer surface 144, and tip circumferential inner surface 146 form a part of the sidewall 124 of the elongate member 118, the circumferential outer surface 126 of the elongate member 118, and circumferential inner surface 128 of the elongate member 118, respectively.

Referring still to FIGS. 3A to 3C, the dilator further includes an EAM electrode 148, which is associated with the dilating tip 134. As described above, the EAM electrode 148 can allow for the location of the dilating tip 134 to be determined, for example the location of the dilating tip 134 within the body, or the location of the dilating tip 134 with respect to other parts of the surgical perforation system 100. The EAM electrode 148 can be, for example, annular, and can be made of or can include stainless steel or platinum-iridium. In some examples, the EAM electrode can additionally be radiopaque, which can allow for visualization of the electrode using fluoroscopy, if desired. In further examples, the EAM electrode can have an echogenic profile, which can allow for visualization of the electrode using ultrasound, if desired. For example, the EAM electrode can include a coil. In some examples, the EAM electrode 148 can be made of a conductive paint.

As mentioned above, the EAM electrode 148 is associated with the dilating tip 134. The term "associated with" indicates that the EAM electrode 148 is positioned to allow for the determination of the location of the dilating tip 134, whether directly (e.g. in cases where the EAM electrode 148 forms all or a part of the dilating tip or in cases where the EAM electrode is mounted directly to the dilating tip 134), or indirectly (e.g. in cases where the EAM electrode 148 is spaced from the dilating tip 134 and where an extrapolation is carried out to determine the location of the dilating tip 134 based on the location of the EAM electrode 148).

In the example shown, the EAM electrode 148 is annular and extends circumferentially around the dilating tip 134, and is positioned between the first end 136 of the dilating tip 134 and the second end 138 of the dilating tip 134. In alternative examples (e.g. as shown in FIGS. 5A to 5D), the EAM electrode can be positioned proximal of the dilating tip, or distal of the dilating tip. In such examples, as mentioned above, an extrapolation can be carried out to determine the location of the dilating tip based on the location of the EAM electrode.

Referring to FIG. 3C, in the example shown, the circumferential outer surface 144 of the dilating tip 134 has a circumferential groove 150 defined therein, and the EAM electrode 148 is seated in the groove 150. The EAM electrode 148 can be secured in the groove 150 in a variety of ways, such as by gluing, welding, soldering, and/or by friction. Furthermore, in the example shown, the EAM electrode 148 is profiled to match the taper of the dilating tip 134, so that the outer surface of the EAM electrode 148 is flush with the circumferential outer surface 144 of the dilating tip 134. This can be achieved, for example, by swaging. This can allow for a smooth transition as the dilating tip 134 is passed through an aperture.

In the example shown, the dilating tip 134 is of a one-piece construction. In alternative examples, as will be described below with reference to FIGS. 4A to 4C, the dilating tip can be of a multi-piece construction.

Referring still to FIGS. 3A to 3C, an electrical conductor 152 is connected to the EAM electrode 148, and extends proximally from the EAM electrode 148 towards the proximal end portion 120 (not shown in FIGS. 3A to 3C) of the elongate member 118, for connection to the EAM signal generator 106 of the EAM system 104 (not shown in FIGS. 3A to 3C). The electrical conductor 152 is electrically insulated between the EAM electrode 148 and its connection to the EAM signal generator 106, so that electrical signals can be communicated between the EAM electrode 148 and the EAM system 104. For example, the electrical conductor 152 can include a layer of polyimide insulation.

The end of the electrical conductor 152 that is connected to the EAM electrode 148 may be referred to herein as the 'electrode end portion 154' of the electrical conductor 152 (shown in FIG. 3C), and the end of the electrical conductor 152 that is connectable to the EAM system 104 may be referred to herein as the 'system end portion 156' of the electrical conductor 152 (shown in FIGS. 1 and 2). The system end portion 156 of the electrical conductor 152 may be connected or connectable to the EAM signal generator 106 in various ways. In the example shown, a connector 158 is mounted to the system end portion 156. The connector 158 is mateable with a connector 160 of the EAM signal generator 106. Alternatively, clips (e.g. alligator clips) may be used to connect the system end portion of the electrical conductor to the EAM system (not shown).

Referring still to FIGS. 3A to 3C, in the example shown, the electrical conductor 152 extends from the EAM electrode 148, through the tip sidewall 142, and into the lumen 130. The electrical conductor 152 then extends through the lumen 130 to the proximal end portion 120 of the elongate member 118. In alternative examples, as will be described below, the electrical conductor can be embedded within the sidewall of the elongate member.

As mentioned above, in the example shown, the EAM system 104 includes the EAM signal generator 106 and a pair of EAM pads 108. Such systems are commercially available, for example under the brand names ENSITE PRECISION™ and CARTO®, and are not described in detail herein. Briefly, by routing electrical signals from the EAM signal generator 106 to the EAM pads 108, from the EAM pads 108 to the EAM electrode 148, and from the EAM electrode 148 back to the EAM signal generator 106 (or in the reverse order—i.e. from the EAM signal generator 106 to the EAM electrode 148, from the EAM electrode 148 to the EAM pads 108, and from the EAM pads 108 back to the EAM signal generator 106), the EAM electrode 148 may be visualized, and thus the location of the dilating tip 134, can be determined. In some examples, the EAM system 104 can be a di-electric open source EAM system (e.g. one available under the brand name KODEX-EPD). In addition to allowing for the determination of a location of the dilating tip of the dilator, such as system can allow for the dilator to be used for anatomical mapping (e.g. to map the geometry of heart chambers) without necessarily contacting heart tissue, as described in further detail below.

In the example shown, the perforation electrode 113 of the RF perforation device 112 can also be used as an additional EAM electrode. That is, together with the EAM electrode 148 of the dilator 102, the perforation electrode 113 of the RF perforation device 112 can be electrically connected to the EAM system 104, so that its location can be determined by the EAM system 104.

Referring now to FIGS. 4A to 4C, an alternative example of a dilating tip is shown. In FIG. 4, features that are like those of FIGS. 1 to 3 will be referred to with like reference numerals, incremented by 300. The dilating tip 434 of FIG. 4 is similar to the dilating tip 134 of FIGS. 1 to 3; however, the dilating tip 434 is of a multi-piece construction. Specifically, in the example shown, the dilating tip 434 includes a proximal piece 462, and a distal piece 464. The proximal piece 462 is stepped to define a distal-facing shoulder surface 466, and has a neck 468 extending distally from the shoulder surface 466. The EAM electrode 448 is annular and is received on the neck 468 and abuts the shoulder surface 466. The distal piece 464 is received on the neck 468 distally of the EAM electrode 448 and abuts the EAM electrode 448. The proximal piece 462, EAM electrode 448, and distal piece 464 can be secured together in a variety of ways, such as by adhering and/or friction.

Referring now to FIGS. 5A to 5D, another alternative example of a dilating tip is shown. In FIG. 5, features that are like those of FIGS. 1 to 3 will be referred to with like reference numerals, incremented by 400. The dilating tip 534 of FIG. 5 is similar to the dilating tip 134 of FIGS. 1 to 3; however, the electrical conductor 552 is embedded in the sidewall 524 of the elongate member 518. Specifically, the circumferential outer surface 526 of the elongate member 518 has a longitudinal groove 570 defined therein. The groove 570 extends from the EAM electrode 548 to the proximal end portion (not shown) of the elongate member 518. The electrical conductor 552 is seated in the groove 570, and a strip of material 572 (e.g. plastic or glue) fills the groove 570 over the electrical conductor 552.

Figure 6A:
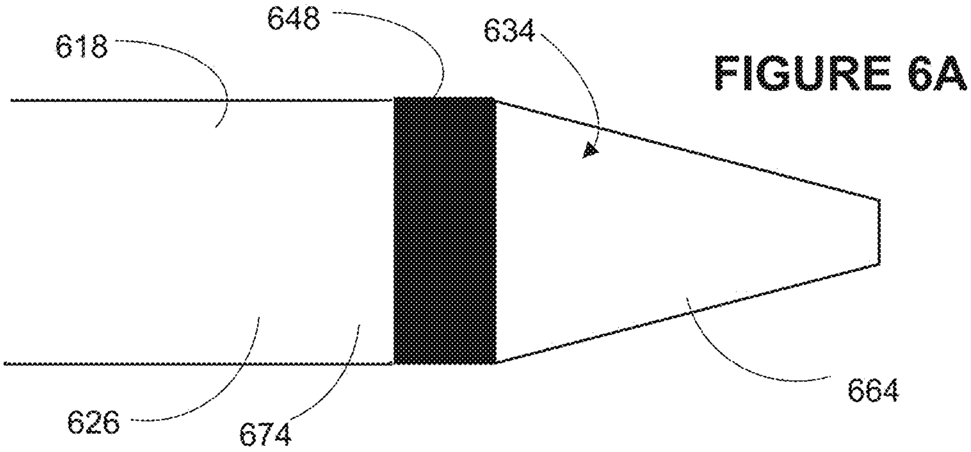
FIG. 6A is an enlarged view of another example dilating tip.
Figure 6B:
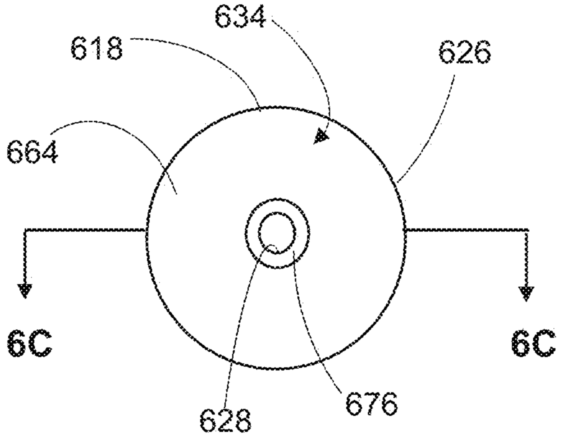
FIG. 6B is an end view of the dilating tip of FIG. 6A.
Figure 6C:
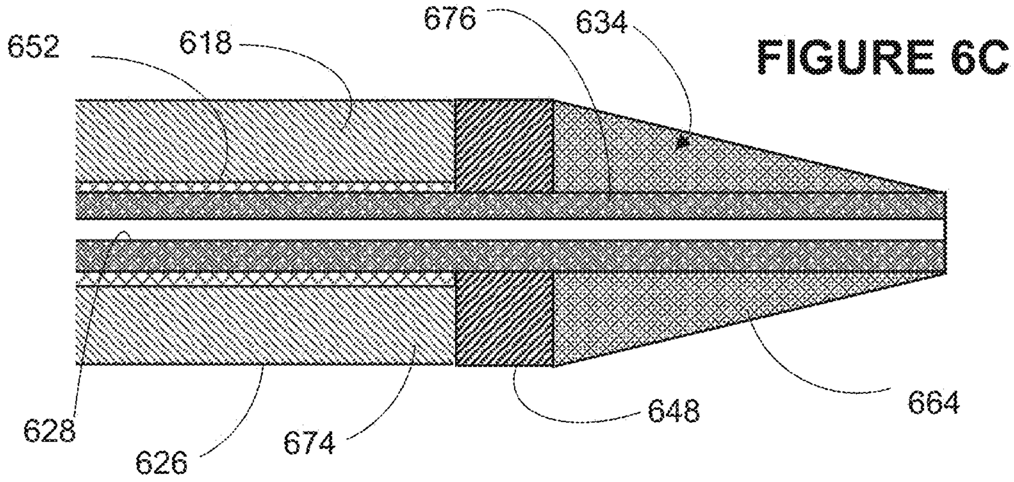
FIG. 6C is a cross-section taken along line 6C-6C in FIG. 6B.

Referring now to FIGS. 6A to 6C, another alternative example of a dilating tip is shown. In FIG. 6, features that are like those of FIGS. 1 to 3 will be referred to with like reference numerals, incremented by 500. The dilating tip 634 of FIG. 6 is similar to the dilator of FIGS. 1 to 3; however, the elongate member 618 includes an outer tube 674, which defines the circumferential outer surface 626, and an inner liner 676 within the outer tube 674, which defines the circumferential inner surface 628. The inner liner 676 can be, for example, a polyimide or polytetrafluoroethylene liner, and the outer tube 674 can be made of a plastic such as HDPE.

In the example of FIG. 6, the electrical conductor 652 is defined by a tubular braid of metallic wires, which is positioned between the outer tube 674 and inner liner 676.

Optionally, in order to fabricate the dilator of FIG. 6, the outer tube 674, electrical conductor 652, EAM electrode 648, and inner liner 676 can first be assembled together, and the EAM electrode 648 can be swaged to form an electrical connection between the EAM electrode 648 and the electrical conductor 652. Then, the material of the outer tube 674 can be re-flowed (e.g. by the application of heat) to join the outer tube 674, electrical conductor 652, and inner liner 676. A distal piece 664 of the dilating tip 634 can then be joined to the assembly. The system end (not shown) of the electrical conductor 652 can then be exposed for connection to the EAM system 104, optionally by skiving.

Figure 7:
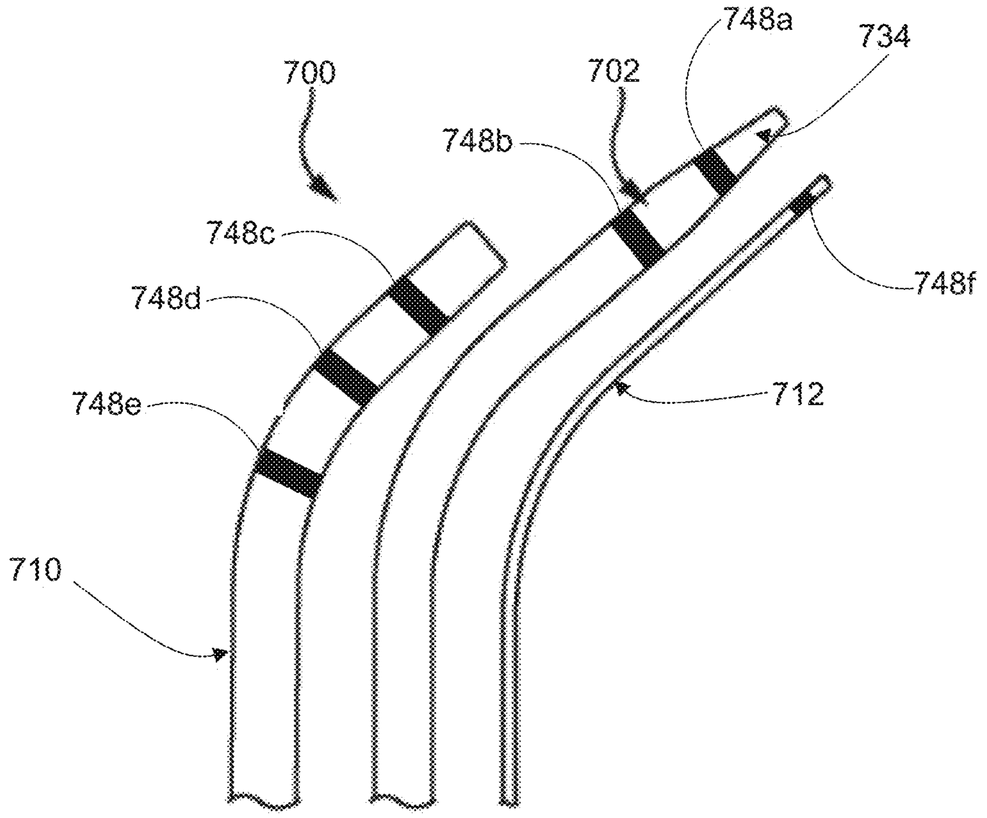
FIG. 7 is a partial perspective view of a sheath, dilator, and perforation device of another example surgical perforation system.

Referring now to FIG. 7, another example of a surgical perforation system is shown. In FIG. 7, features that are like those of FIG. 1 will be referred to with like reference numerals, incremented by 600. In FIG. 7, only the dilator 702, sheath 710, and RF perforation device 712 of the system 700 are shown; the remaining parts of the system 700 can be the same as or similar to the parts shown in FIG. 1. The system 700 of FIG. 7 includes additional EAM electrodes. Specifically, the system 700 includes a first EAM electrode 748*a* associated with the dilating tip, as described above with respect to FIGS. 1 to 3. Additionally, the system includes a second EAM electrode 748*b* on the dilator 702 and spaced from the first EAM electrode 748*a*; third 748*c*, fourth 748*d*, and fifth 748*e* EAM electrodes on the sheath 710; and a sixth EAM electrode 748*f* on the RF perforation device 712. The second through sixth EAM electrodes (748*b*-748*f*) are connectable to the EAM signal generator via additional electrical conductors (not shown). The use of additional EAM electrodes can allow for additional location data to be determined. For example, the location of the sheath 710, or the location dilating tip 734 with respect to the sheath 710, can be determined. Additionally, by providing additional electrodes, the orientation of the sheath or dilator may be determined. For example, providing at least two electrodes on each of the sheath and dilator allows the determination of the direction in which the devices are oriented.

In another example (not shown), a dilator can be similar to the dilator 702 of FIG. 7; however the second EAM electrode can be positioned so that when the dilator is fully inserted into the sheath, the second EAM electrode is proximate the tip of the sheath (e.g. flush with or close to flush with the tip of the sheath). In such examples, even if the sheath itself does not include any EAM electrodes, the second EAM electrode of the dilator can be used to determine a location of the tip of the sheath when the dilator is fully inserted into the sheath. For example, the second EAM electrode of the dilator can be used to determine whether tip of the sheath has entered the left atrium during a transseptal perforation procedure.

Figure 14A:
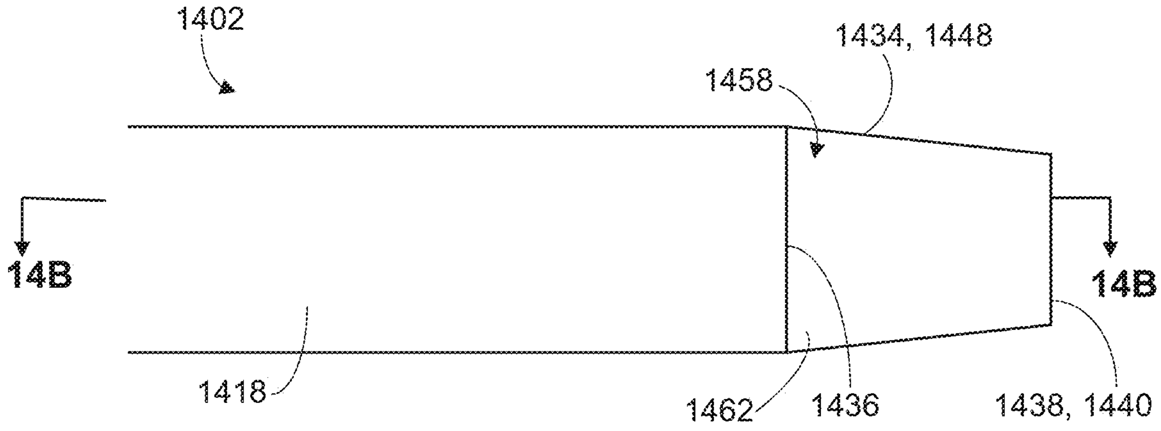
FIG. 14A is a partial side view of another example dilator.
Figure 14B:
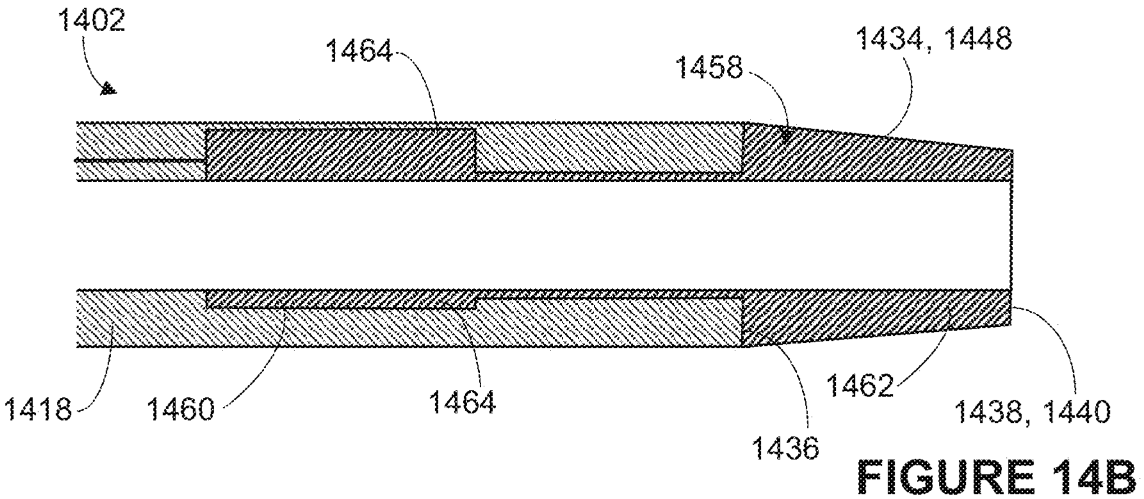
FIG. 14B is a cross-section taken along line 14B-14B in FIG. 14A.
Figure 14C:
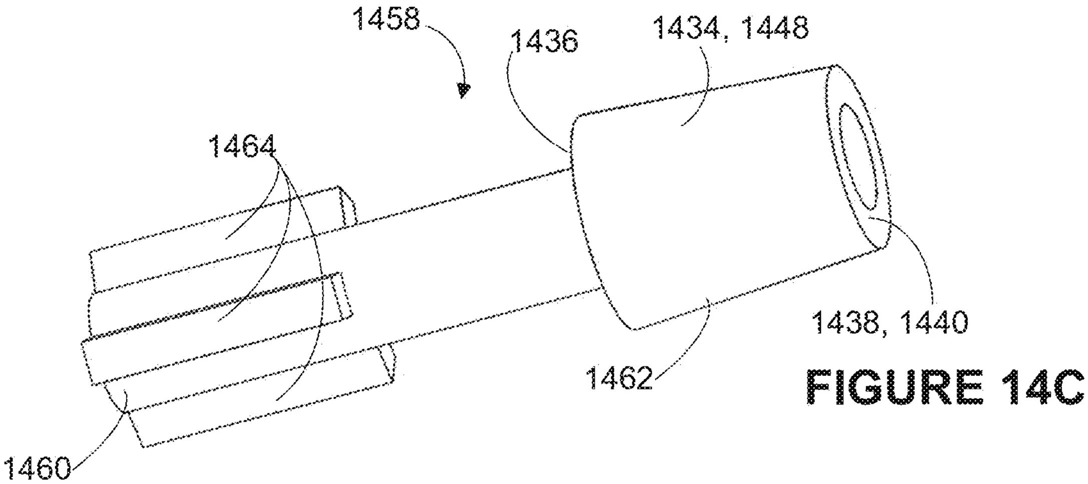
FIG. 14C is a perspective view of the metallic member of the dilator of FIG. 14A.

Referring now to FIGS. 14A to 14C, another example of a dilator is shown. In FIGS. 14A to 14C, features that are like those of FIGS. 1 to 3 will be referred to with like reference numerals, incremented by 1300. In the dilator 1402, the dilating tip 1434 is similar to the dilating tip 134 of FIGS. 1 to 3; however, the EAM electrode 1448 forms the dilating tip 1434. That is, a metallic member 1458 (shown in isolation in FIG. 14C) is provided that includes a first section 1460 and a second section 1462. The first section 1460 secures the metallic member 1458 to the elongate member 1418, while the second section 1462 serves as the EAM electrode 1448 and also forms the dilating tip 1434. The first section 1460 includes ribs 1464 that are embedded in the elongate member 1418, to secure the metallic member 1458 to the elongate member 1418. The second section 1462 extends distally from the first section 1460, and tapers in cross-sectional area going from a first end 1436 thereof to a second end thereof 1438, to form the dilating tip 1434. In this example, the EAM electrode 1448 forms the distal end 1440 of the dilator 1402, and therefore can allow for tissue contact with the EAM electrode.

In a further alternative example of a dilator (not shown), the EAM electrode can be removable from the elongate member. For example, the elongate member of the dilator can be a standard dilator (e.g. one known in the art). The EAM electrode, connected to the electrical conductor, can be separate from the elongate member. For example, the EAM electrode can be secured to the perforation device. The EAM electrode can be advanced through the lumen of the elongate member, until the EAM electrode is at the distal end of the dilator. The assembly can be calibrated so that the extent to which the EAM electrode should be advanced to reach the distal end is known.

Referring now to FIGS. 8 to 13, a method for medical dilation, specifically for creation and dilation of a transseptal perforation, will be described. As will be described in more detail, at various points during the method, the EAM electrode and EAM system can be engaged to determine the location of the dilating tip of the dilator—i.e. EAM signals can be received from the EAM electrode of the dilator, and based on the EAM signals, the location of the dilating tip of the dilator can be determined, and optionally mapped and tracked. This can enhance safety of the procedure. The method will be described with reference to the system 100 and dilator 102 as shown in FIGS. 1 to 3; however, the method is not limited to being carried out with system 100 and dilator 102, and the system 100 and dilator 102 are not limited to use according to the described method.

Figure 8:
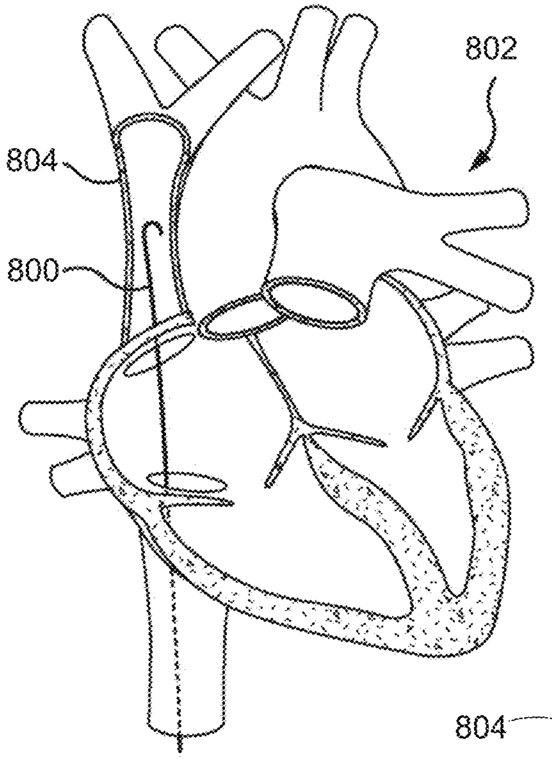
FIG. 8 is a schematic view showing a first step of an example method for creation and dilation of a transseptal perforation.

Referring to FIG. 8, a guidewire 800 can be advanced via the femoral vein towards the heart 802, and "parked" in the superior vena cava (SVC) 804.

Figure 9:
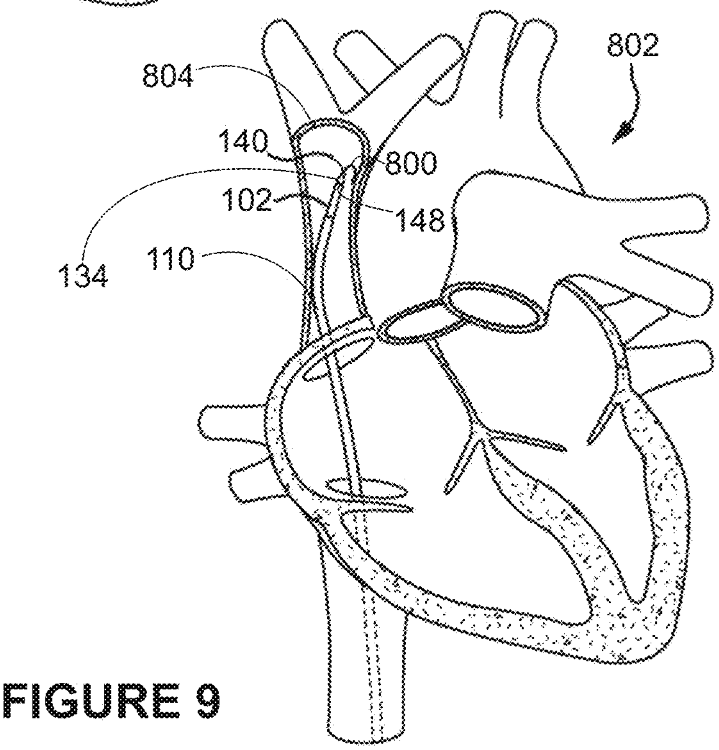
FIG. 9 is a schematic view showing a second step of the example method for creation and dilation of a transseptal perforation of FIG. 8.

Referring to FIG. 9, with the dilator 102 in the sheath 110, and with the dilating tip 134 extending proud of the sheath 110, the dilator 102 and sheath 110 can be advanced over the guidewire 800 towards the SVC 804. The guidewire 800 can then be removed, and the RF perforation device 112 (not shown in FIG. 9) can be advanced through the dilator 102 until the perforation electrode 113 (not shown in FIG. 9) of the RF perforation device 112 is just shy of the distal end 140 of the dilator 102.

As mentioned above, in addition to the EAM electrode 148 of the dilator 102 being connected to the EAM system 104 (not shown in FIGS. 8 to 13), the perforation electrode 113 of the RF perforation device 112 can be connected to the EAM system 104 and can serve as an additional EAM electrode. After the RF perforation device 112 has been advanced through the dilator 102 and the perforation electrode 113 is exposed from the dilator 102 or the distal tip of the perforation device 112 is flush with the distal tip of the dilator 102, the positioning of the perforation device 112 can be confirmed using the EAM system 104. Specifically, the EAM system 104 can be engaged, and based on the EAM signal received from the EAM electrode 148 and the perforation electrode 113, the location of the perforation electrode 113 with respect to the dilating tip 134 can be determined. For example, if the EAM system shows that the perforation electrode 113 is proud of the dilating tip 134, it can be determined that the perforation electrode 113 has been advanced too far into the dilator 102. Alternatively, if the perforation electrode 113 cannot be detected by the EAM system, it can be concluded that the perforation electrode 113 is shrouded within the dilating tip 134, and therefore correctly positioned. Additionally, by providing both a perforation electrode 113 and an EAM electrode 148, the relative positioning between the two may be mapped to allow determination of the orientation of the combined assembly.

In some examples, the system 100 can further be configured to provide an alert if the perforation electrode 113 advances distal of the distal end 140 of the dilator 102.

Optionally, at this point, if anatomical data is desired, the user can refer to CT or MRI data.

Figure 10:
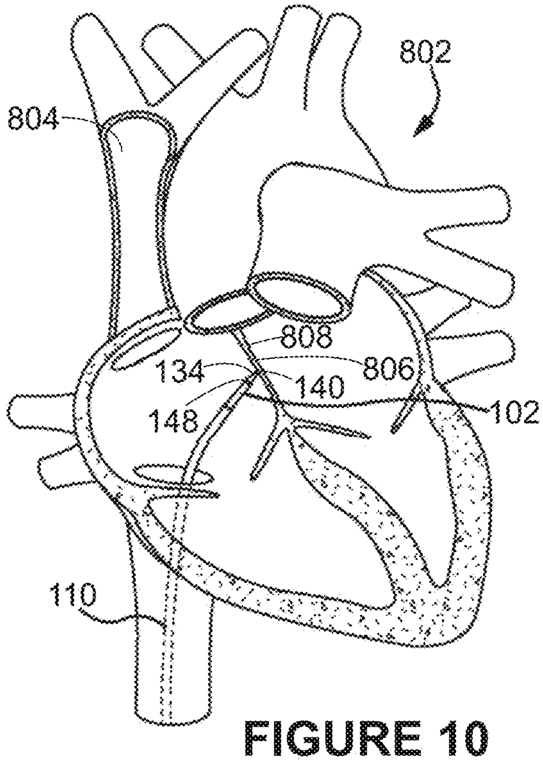
FIG. 10 is a schematic view showing a third step of the example method for creation and dilation of a transseptal perforation of FIG. 8.

Referring now to FIG. 10, with the EAM electrode 148 and EAM system 104 engaged to track the location of the dilating tip 134 and the perforation electrode 113 (not shown in FIG. 10), the sheath 110, dilator 102, and perforation device 112 can be advanced towards a target anatomical location to position the dilating tip 134 at the target location. The target anatomical location can be, for example, the fossa ovalis 806 of the atrial septum 808. The EAM electrode 148 and EAM system 104 can be used to confirm the positioning of the dilating tip 134 against the fossa ovalis 806, and also to confirm that the perforation electrode 113 is flush with the distal end 140 of the dilator 102.

Figure 11:
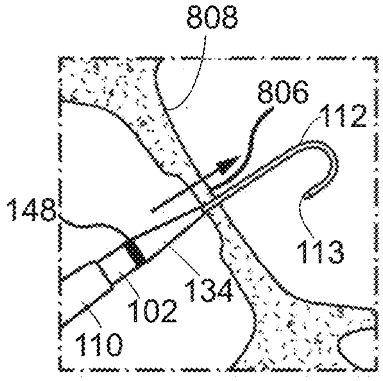
FIG. 11 is a schematic view showing a fourth step of the example method for creation and dilation of a transseptal perforation of FIG. 8.

Referring to FIG. 11, the perforation device 112 can then be engaged and advanced out of the dilator 102, to create a perforation in the atrial septum 808.

Figure 12:
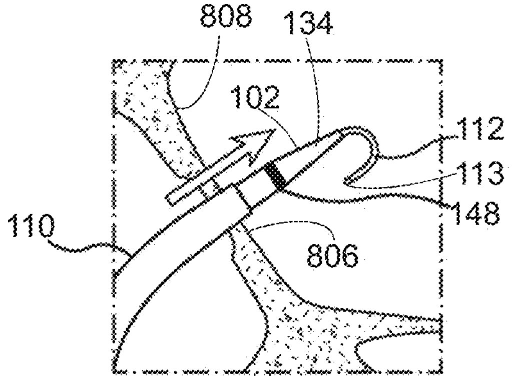
FIG. 12 is a schematic view showing a fifth step of the example method for creation and dilation of a transseptal perforation of FIG. 8.

Referring to FIG. 12, the dilating tip 134 can then be advanced through the perforation, to dilate the perforation. Specifically, the dilating tip 134, together with the EAM electrode 148, can be advanced through the perforation. Prior to, during and/or after advancement of the dilating tip 134 and EAM electrode 148, the EAM electrode 148 and EAM system 104 can be engaged to determine the location of the dilating tip 134. This can help to ensure that the perforation is sufficiently dilated, while also helping to ensure that the dilating tip 134 does not contact and thereby damage non-target tissues (e.g. the location of the dilating tip with respect to the left atrial wall can be visualized).

Figure 13:
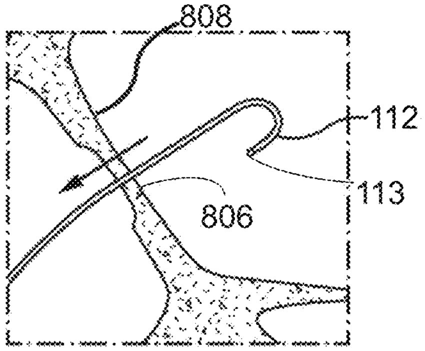
FIG. 13 is a schematic view showing a second step of the example method for creation and dilation of a transseptal perforation of FIG. 8.

Following dilation of the perforation, various procedures can be carried out. At the desired time, as shown in FIG. 13, the dilator 102 and sheath 110 can be withdrawn from the heart 802. Optionally, during withdrawal, the EAM electrode 148 and EAM system 104 can be engaged, to determine the location of the dilating tip 134.

Optionally, throughout the method, anatomical mapping can be carried out using the dilator 1402 and the EAM system 104. That is, as mentioned above, if the EAM system 104 is a dielectric open source EAM system, the dilator 102 and EAM system 104 can be used for cardiac mapping, without necessarily contacting any cardiac tissue. For example, during advancement of the dilator 102, when the dilator 102 is in the inferior vena cava, the EAM system 104 can be engaged (i.e., a electroanatomical signal can be received from the EAM electrode 148) to map the SVC 804. For further example, when the dilator 102 is in the right atrium 808, the EAM system 104 can be engaged to map the right atrium 808. For further example, after the dilator 102 crosses the atrial septum 808, the EAM system 104 can be engaged to map the pulmonary veins. This can be facilitated by rotating the dilator 102. In such examples, as the dilator 102 advances towards a location that is to be mapped, more detail and increasing resolution may be achieved. Furthermore, in examples where the EAM electrode is at the distal end of the dilator, the EAM system may be able to provide an alert when tissue is contacted by the distal end of the dilator.

While the above description provides examples of one or more processes or apparatuses or compositions, it will be appreciated that other processes or apparatuses or compositions may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

We claim:

1. A medical dilator, comprising:

an elongate member having a proximal end portion, an opposed distal end portion, and a lumen extending through the elongate member from the proximal end portion to the distal end portion;

a dilating tip at the distal end portion, the dilating tip having a first end of enlarged cross-sectional area and tapering going in the distal direction to a second end of reduced cross-sectional area, the dilating tip comprising a proximal piece having a distal-facing shoulder surface and a neck extending distally from the shoulder surface;

at least a first electrode associated with the dilating tip; and an electrical conductor electrically connected to the first electrode and extending proximally from the first electrode towards the proximal end portion for electrical connection with an electroanatomical mapping system;

wherein the first electrode is annular and is received on the neck and abuts the shoulder surface; and wherein the dilating tip further comprises a distal piece received on the neck distally of and abutting the first electrode.

2. The medical dilator of claim 1, wherein the first electrode is positioned between the first end of the dilating tip and the second end of the dilating tip.

3. The medical dilator of claim 1, wherein the first electrode is positioned proximal of the first end of the dilating tip.

4. The medical dilator of claim 1, wherein the first electrode has an electrode outer surface, and the electrode outer surface is flush with a tip circumferential outer surface of the dilating tip.

5. The medical dilator of claim 1, wherein the dilating tip has a tip circumferential outer surface, a tip circumferential inner surface, and a tip sidewall extending between the tip circumferential inner surface and the tip circumferential outer surface, and the electrical conductor extends from the first electrode through the tip sidewall and into the lumen.

6. The medical dilator of claim 1, wherein the elongate member has a circumferential outer surface, a circumferential inner surface, and a sidewall extending along the length of the elongate member between the circumferential inner surface and the circumferential outer surface, and the electrical conductor is embedded in the sidewall and extends from the first electrode to the proximal end portion.

7. The medical dilator of claim 6, wherein the circumferential outer surface has a longitudinal groove defined therein and extending from the first electrode to the proximal end portion, and wherein the electrical conductor is seated in the longitudinal groove.

8. The medical dilator of claim 6, wherein the elongate member comprises an outer tube defining the circumferential outer surface, and an inner liner within the outer tube and defining the circumferential inner surface, and wherein the electrical conductor is a tubular braid and is positioned between the outer tube and the inner liner.

9. The medical dilator of claim 1, wherein the first electrode is radiopaque or has an echogenic profile.

10. A medical dilation system, comprising:

a medical dilator comprising an elongate member having a proximal end portion, an opposed distal end portion, and a lumen extending through the elongate member from the proximal end portion to the distal end portion; a dilating tip at the distal end portion, the dilating tip having a first end of enlarged cross-sectional area and tapering going in the distal direction to a second end of reduced cross-sectional area, the dilating tip comprising a proximal piece having a distal-facing shoulder surface and a neck extending distally from the shoulder surface; at least a first electrode associated with the dilating tip; and an electrical conductor electrically connected to the first electrode and extending proximally from the first electrode to the proximal end portion; and an electroanatomical mapping system electrically connectable to the electrical conductor and configured to receive an electroanatomical mapping signal from the electrode and determine a location of the dilating tip based on the electroanatomical mapping signal;

wherein the first electrode is annular and is received on the neck and abuts the shoulder surface; and wherein the dilating tip further comprises a distal piece received on the neck distally of and abutting the first electrode.

11. The medical dilation system of claim 10, wherein the electroanatomical mapping system is a dielectric open source system.

* * * * *